US008274655B2

(12) United States Patent
Herzog

(10) Patent No.: US 8,274,655 B2
(45) Date of Patent: Sep. 25, 2012

(54) METHOD AND SYSTEM FOR IN SITU AEROSOL THERMO-RADIOMETRIC ANALYSIS

(75) Inventor: William D. Herzog, Groton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 315 days.

(21) Appl. No.: 12/697,399

(22) Filed: Feb. 1, 2010

(65) Prior Publication Data
US 2010/0220323 A1 Sep. 2, 2010

Related U.S. Application Data

(60) Provisional application No. 61/150,123, filed on Feb. 5, 2009.

(51) Int. Cl.
*G01N 15/02* (2006.01)
(52) U.S. Cl. ........................................ 356/336
(58) Field of Classification Search .................. None
See application file for complete search history.

(56) References Cited

U.S. PATENT DOCUMENTS

| 5,920,388 | A | 7/1999 | Sandberg et al. |
| 6,694,799 | B2 * | 2/2004 | Small ........................ 73/24.02 |
| 7,667,840 | B2 * | 2/2010 | Otsuki et al. ................ 356/338 |
| 7,770,432 | B2 * | 8/2010 | Roesch et al. ............... 73/23.33 |

FOREIGN PATENT DOCUMENTS

| JP | 61-040537 | 2/1986 |
| JP | 62-191054 | 8/1987 |
| JP | 63-224711 | 9/1988 |
| JP | 63-286753 | 11/1988 |
| JP | 63-302342 | 12/1988 |
| JP | 01-015635 | 1/1989 |
| JP | 01-015636 | 1/1989 |
| JP | 01-015638 | 1/1989 |
| JP | 01015634 | 1/1989 |
| JP | 01-281121 | 11/1989 |
| JP | 03-064611 | 3/1991 |
| JP | 04-135619 | 5/1992 |

(Continued)

OTHER PUBLICATIONS

Jennings, et al., "Volatility of Aerosol at Mace Head, On the West Cost of Ireland," *Journal of Geophysical Research*, vol. 95, No. D9, pp. 13,937-13,948 (Aug. 20, 1990).

(Continued)

*Primary Examiner* — Tu Nguyen
(74) *Attorney, Agent, or Firm* — Foley & Lardner LLP

(57) ABSTRACT

Particle detection systems configured to identify a particle in a bulk sample volume are less efficient than those configured to measure a single particle. A particle detection system according to an inventive embodiment can identify a particle in a fluid stream. The detection system may employ one or more heating stations. Each heating station may be set to a distinct temperature. The heating stations may include a light source and a light detector, such that once a particle traverses a beam provided by the light source, the light detector may measure resultant optical scattering. Based on the optical scattering with respect to temperature or temperature variation, an identification of the single particle may be obtained, thereby eliminating measurement inaccuracies associated with bulk sample volumes. The particle detection system may detect organic particles among inorganic particles in various fluid flow environments, such as for safety or quality purposes.

29 Claims, 9 Drawing Sheets

FOREIGN PATENT DOCUMENTS

| JP | 04-283648 | 10/1992 |
|----|-----------|---------|
| JP | 05-322739 | 12/1993 |
| JP | 05-322740 | 12/1993 |
| JP | 09-203703 | 8/1997 |
| JP | 2000-146843 | 5/2000 |
| JP | 2001-027598 | 1/2001 |

OTHER PUBLICATIONS

Pinnick, et al., "Volatility of Aerosols in the Arid Southwestern United States," *Journal of the Atmospheric Sciences*, vol. 44, No. 3, pp. 562-576 (Sep. 19, 1986).

Spjut, et al., "Electrodynamic Thermogravimetric Analyzer," *Rev. Sci. Instrum.*, vol. 57, No. 8, pp. 1604-1610 (Aug. 1986).

Haboub, A., et al. "Thermal volatilization properties of atmospheric nanoparticles", *Environ Monit Assess* (2007) 134: 191-197 (Apr. 26, 2007).

Notification of Transmittal of the International Search Report and the Written Opinion of the International Searching Authority, or the Declaration from International Application No. PCT/US2010/022712, Date of Mailing Feb. 8, 2011.

* cited by examiner

FIG. 2

METHOD AND SYSTEM FOR IN SITU AEROSOL THERMO-RADIOMETRIC ANALYSIS

RELATED APPLICATIONS

This application claims the benefit of U.S. Provisional Application No. 61/150,123, filed on Feb. 5, 2009, the entire teachings of which are incorporated herein by reference.

GOVERNMENT SUPPORT

The invention was supported, in whole or in part, by a grant FA8721-05-C-0002 from United States Air Force. The Government has certain rights in the invention.

BACKGROUND OF THE INVENTION

The detection and discrimination of types of aerosols has utility in public health monitoring, occupational health monitoring, biological and chemical defense sensing, and industrial production monitoring. For many of these applications it is desirable to be able to measure and discriminate aerosols that form a minority population of an ensemble aerosol, which may include organic, inorganic, and/or biological particles, as well as other particles known in the art. In these cases it is often useful to measure individual aerosol particles for detection and classification.

Prior aerosol instruments typically measure very small concentrations of aerosols, such as single aerosol particles in a liter of air, in a background of a very large number of ambient aerosol particles, which may be as numerous as hundreds to thousands of particles per liter of air. Some instruments of this type simply measure the particle size through optical scattering or aerodynamic means. Other instruments use fluorescence or scattering at multiple visible wavelengths to classify particles. Many of these instruments measure individual aerosol particles one at a time in a very rapid fashion rather than measuring mixtures, or ensembles, of aerosol particles.

Thus, there is a need for an in-situ aerosol sensor that can detect and classify multiple types of aerosols in a rapid, inexpensive manner.

SUMMARY OF THE INVENTION

In example embodiments, a system, and corresponding method for use, may include a particle identifier for identifying a particle in a flow. The particle identifier may include a quantifying unit that may be configured to quantify an optical scattering of the particle as a function of particle temperature across multiple temperatures, each of which is above ambient temperature. The particle temperature is at or near a temperature of atmosphere surrounding the particle (i.e., the particle is at or near atmospheric temperature). The identifier may also include a characterizing unit, which may be configured to characterize a change in size or complex index of refraction of the particle as a function of the optical scattering as quantified across the multiple temperatures, and an identifying unit, which may configured to identify the particle based on characterized change in optical scattering of the particle.

The quantifying unit may be further configured to quantify the optical scattering in a non-binary manner. The quantifying unit may be further configured to receive optical scattering data from a single detector.

The identifier may be configured to analyze the particle in situ. The multiple temperatures may be provided with a series of independent heating stations arranged in order of increasing temperature. A maximum temperature of the multiple temperatures may be a temperature at which an organic particle approaches combustion or vaporization.

The quantifying unit, characterizing unit, and identifying unit may be configured to quantify, characterize, and identify, respectively, the particle after the particle passes through each heating station in a series of heating stations. Each heating station may include a single light sensor, light source, and heat source.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 2 is a schematic diagram of a multiple aerosol particle volatility analyzer;

DETAILED DESCRIPTION OF THE INVENTION

A description of example embodiments of the invention follows.

Many methods of identifying a particle in a particle detection system exist. Typically, particle detection systems are based on particle illumination, or scattering. Particle detection systems based on a particle's thermal responses are also employed in the art for bulk samples of aerosol particles.

Figure 1:
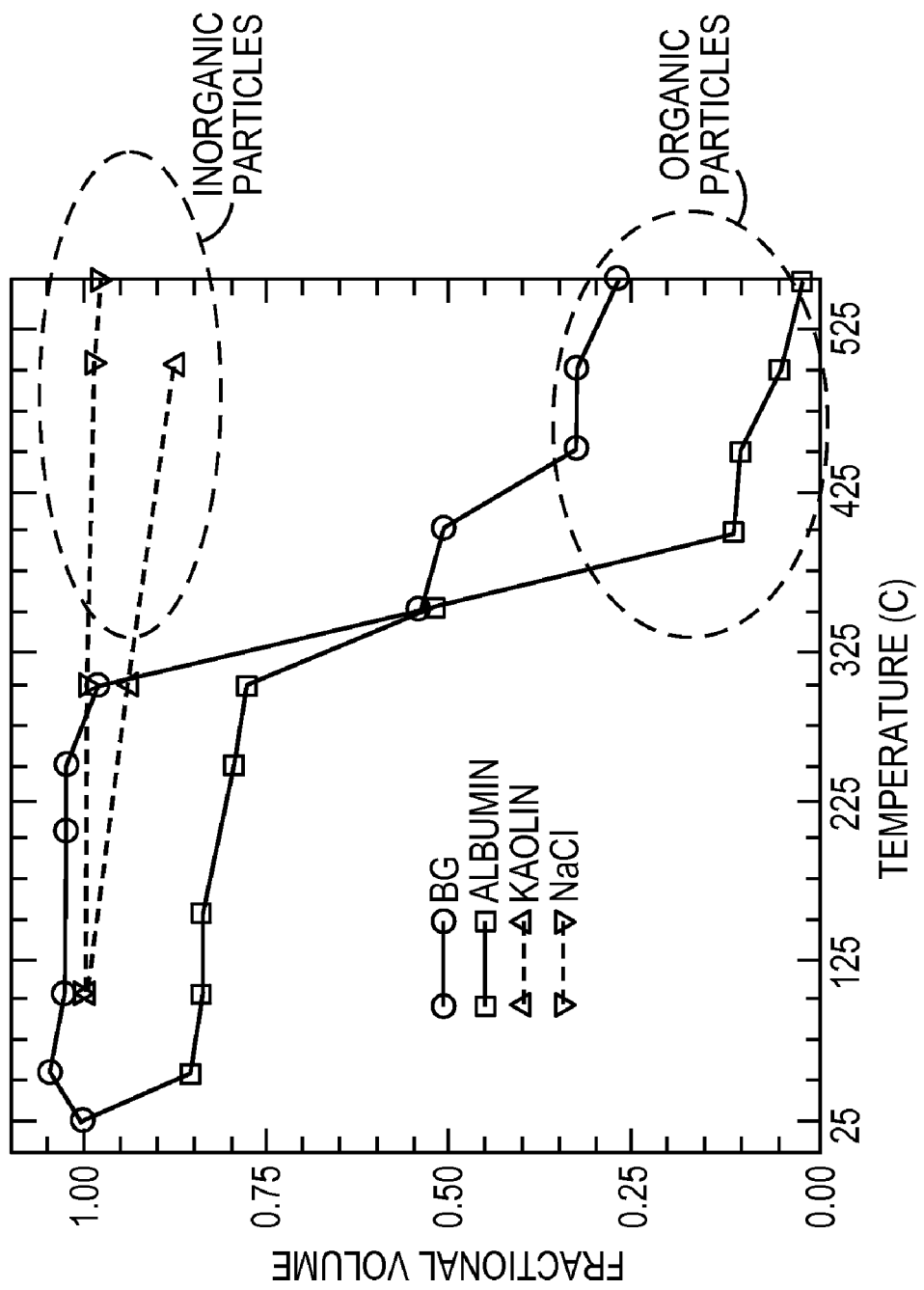
FIG. 1 is a graphical depiction of differences in reaction of inorganic and organic particles with respect to changes in temperature.

FIG. 1 illustrates a difference in thermal responses of inorganic and organic particles in a bulk sample as measured with a traditional thermo-gravimetric analyzer (TGA). As shown, in a temperature range (x-axis) of approximately 125° C. to about 550° C., the inorganic particles, such as Kaolin and sodium chloride (NaCl), experience a little or no reduction in fractional volume (y-axis). In contrast, the organic particles, such as Bacillus Globigii (BG) and Albumin, experience a much greater fractional volume reduction within a temperature range of approximately 25° C. to about 550° C. The organic particles evaporate or reduce in volume at much lower temperatures as compared to inorganic particles.

As is known in the art, a traditional thermo-gravimetric analyzer (TGA) system performs measurements on a bulk sample. If applied to aerosol particles, the bulk sample includes a variety, or mixture, of both organic and inorganic particles. The bulk sample is placed on a scale within a temperature controlled oven. The TGA may perform a number of measurements of the weight of the bulk sample for a number of temperatures. As explained above in reference to FIG. 1, organic and inorganic particles vaporize or combust at different temperatures. Therefore, the resulting bulk sample includes particles that may have vaporized or experienced a reduction in size with an increase in temperature. The weight of the bulk sample may decrease with an increase in temperature. The TGA measurement will not differentiate between the case where many of the particles in the mixture slightly decreased in weight with an increase in temperature and the case where a very small number of the particles in the mixture lost most of their weight.

Figure 2:
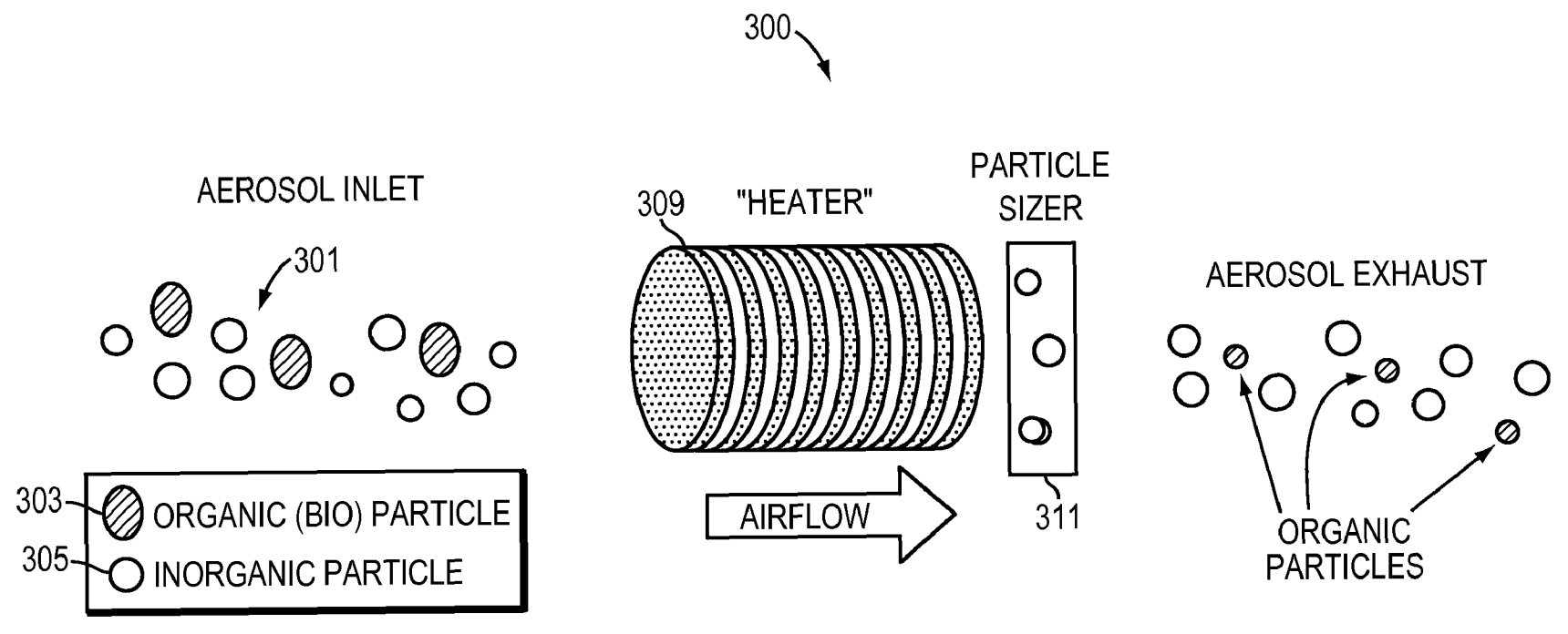

FIG. 2 provides an illustrative example of a multi-particle detection system 300 for volatility analysis of aerosol particles. Multiple aerosol particles including organic 303 and inorganic 305 particles enter a heated oven 309. The oven may be heated to a predetermined temperature. Upon exiting the heated oven 309, the resultant bulk particle sample 313 is measured by a particle sizer 311 (e.g., a nephelometer or a particle counter with size measurement capability). The particle sizer 311 may provide a measurement of the diameter of the different particles in the bulk sample 301 upon being heated via the oven 309. Thus, through various cycles of different oven temperatures, an approximation of the effect of particle diameter due to temperature may be obtained.

However, the volatility analysis, or calculated decrease in diameter due to temperature, may be severely inaccurate for the same reason discussed for bulk TGA measurements of particle mixtures. As the organic particles decrease in size or combust, the inorganic particles may also see a reduction in size. Although the inorganic particle size reduction may be much less than that of the organic particle, the cumulative effect of the size reduction of all inorganic particles in the bulk sample may skew any calculations provided by measured data. Specifically, it may be difficult to ascertain what percentage of the difference in measured results is due to the combustion of inorganic particles or the size reduction of organic particles. Thus, an inorganic particle which has reduced in size may appear as an organic particle which has undergone little or no changes in diameter size. Therefore, in an example embodiment presented herein below, a system capable of measuring a single particle is provided. By utilizing measurements of a single particle, effects of the particle's diameter due to temperature size may be accurately obtained.

Figure 3:
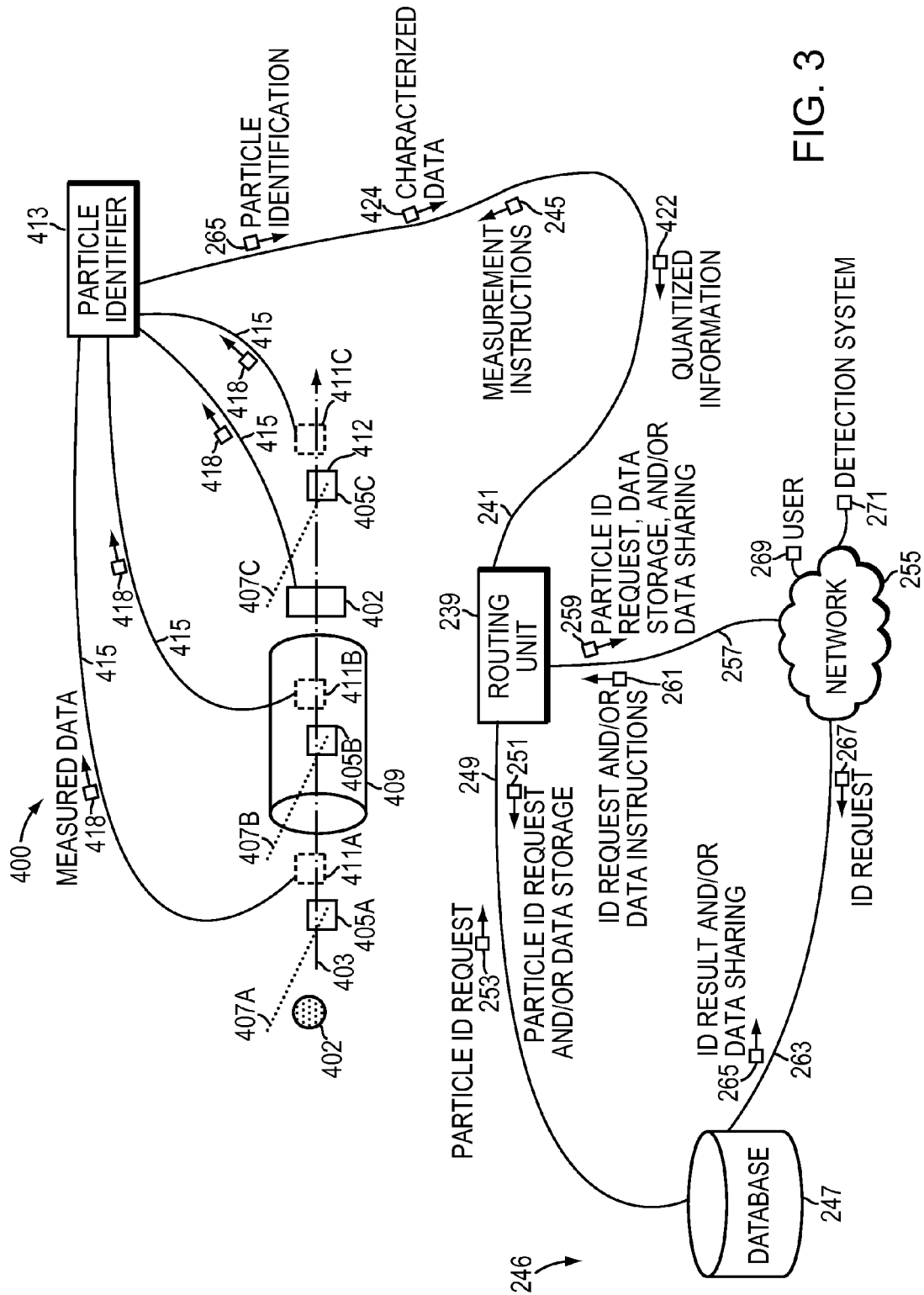
FIG. 3 is a schematic of a single aerosol and single stage particle detection system, featuring a particle identifier, according to example embodiments of the present invention.
Figure 4:
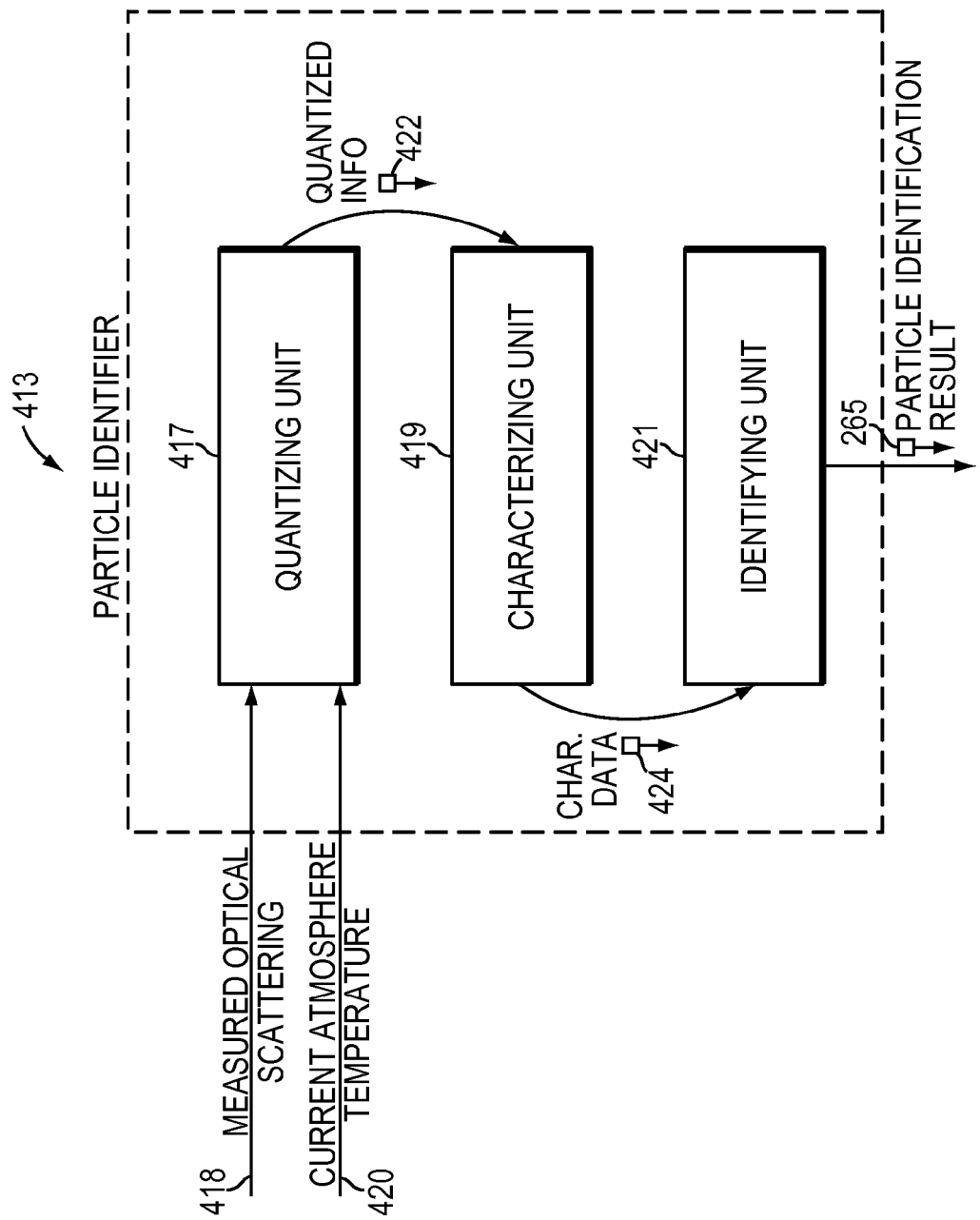
FIG. 4 is a schematic of the particle identifier of FIG. 3 according to an example embodiments of the present invention.
Figure 5:
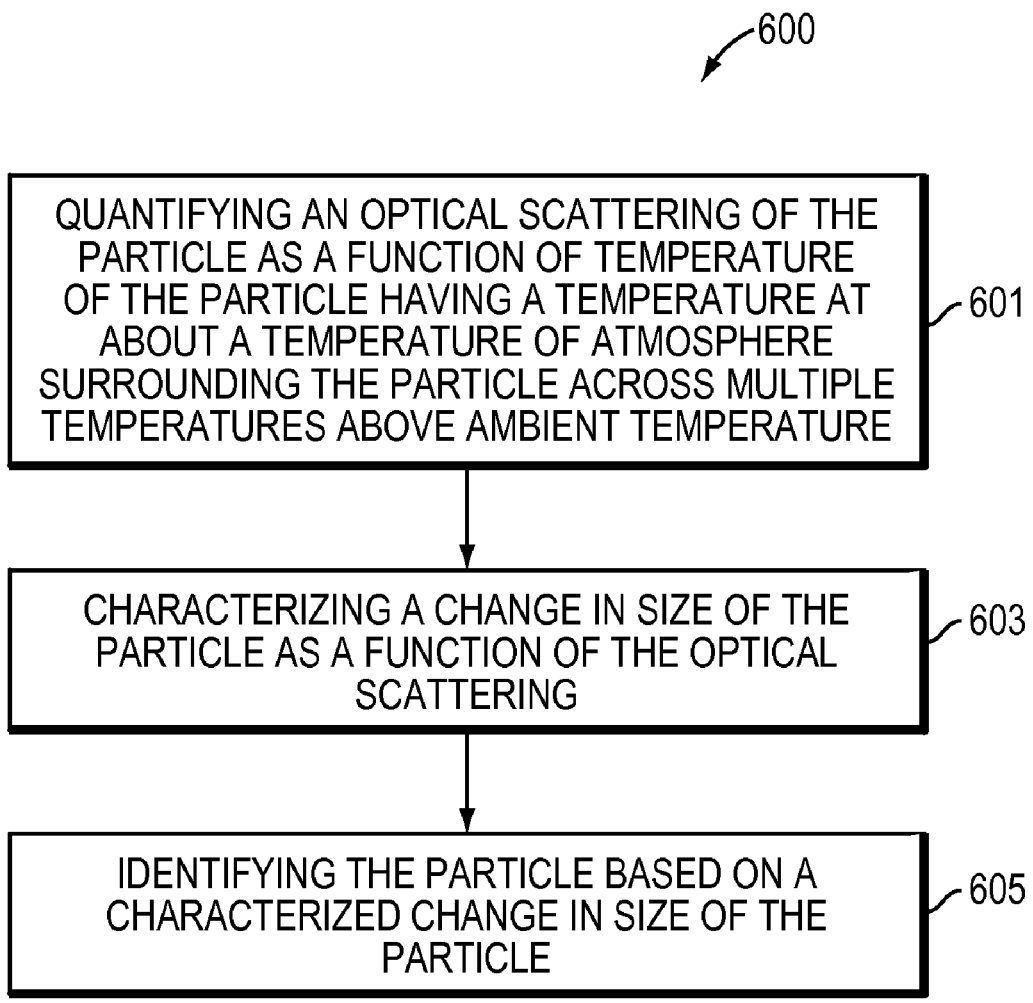
FIG. 5 is a flow diagram depicting example operations of the detection system of FIGS. 3 and 4 according to an example embodiment of the present invention.
Figure 6:
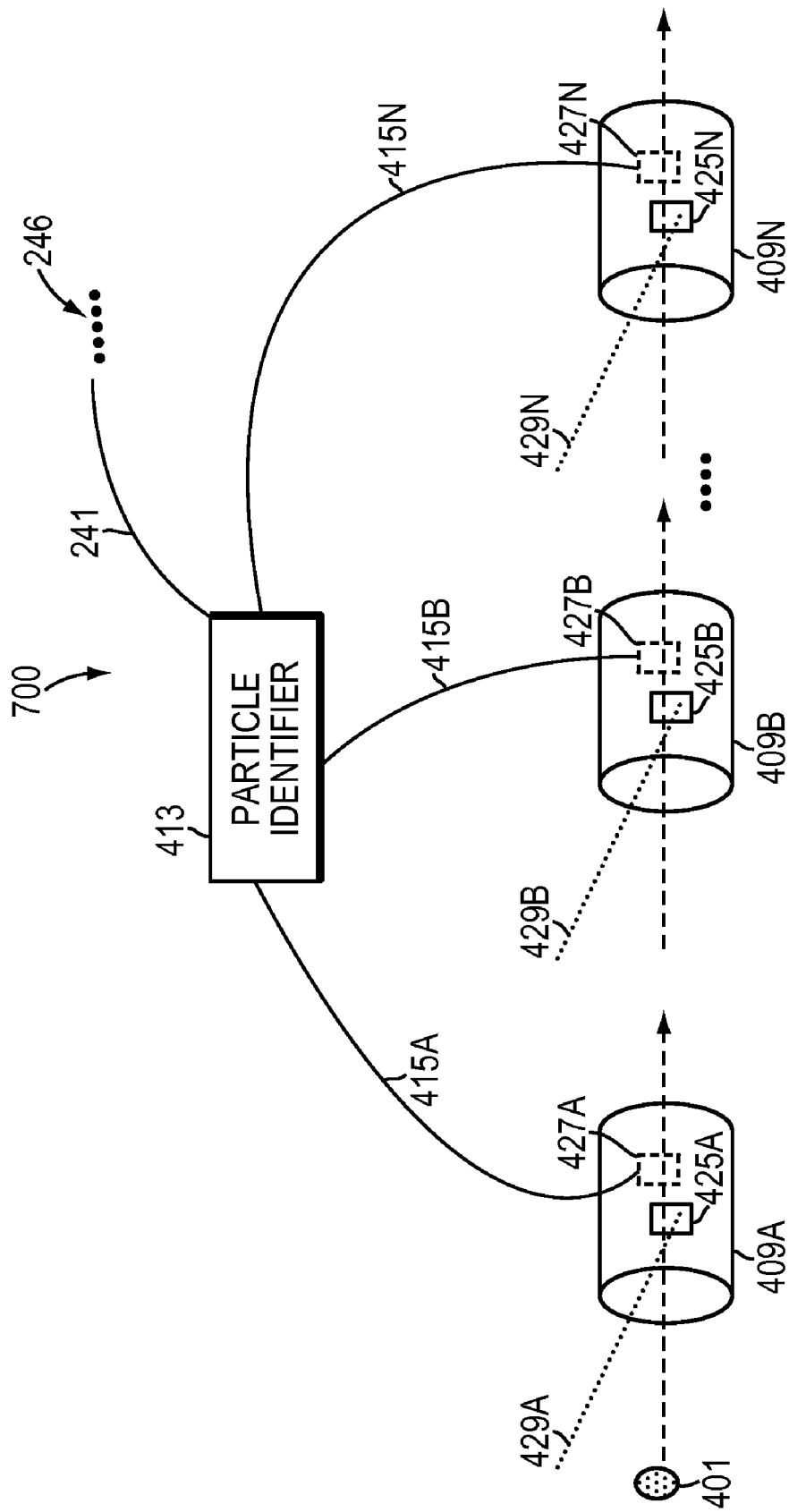
FIG. 6 is a multiple stage, single aerosol particle detection system according to example embodiment of the present invention.

Together, FIGS. 3-5 illustrate a system and method of identifying particles according to example embodiments of the present invention. FIG. 3 shows a particle detection system 400, FIG. 4 is a diagram of the particle identifier 413 shown in FIG. 3, and FIG. 6 shows a flow chart 600 of example operations that may be taken by the particle identifier of FIGS. 3 and 4.

FIG. 3 illustrates a single particle detection system 400 according to an example embodiment. A single particle 401 traveling in a fluid stream 403 (e.g., air or other gas) may be configured to enter a heating station 409. The temperature of the heating station 409 may be adjusted to a temperature between room temperature and a temperature at which a typical organic particle may combust or vaporize. The heating station 409 may also include any number of light sources 405A-C placed at the entrance, within, or near the exit of the heat station 409, respectively. The light sources 405A-C may be configured to provide a propagating light beams 407A-C, respectively. The light sources 405A-C may be coherent or incoherent light sources. The light sources 405A-C may be laser diodes or any other device known in the art for providing light. The heating station 409 may also include any number of light detectors 411A-C, which may be placed so as to detect the light that scatters from the aerosol particle as the particle 401 traverses the light beams 407A-C, respectively. The light detectors 411A-C may be photo-detectors or any other means of light detection known in the art.

In operation, the light scattered from the particle may first be measured at ambient temperature via the light source 405A and light detector 411A situated at the entrance of the heating station 409. As the single particle 401 enters the heating station 409, the particle may come into equilibrium with the temperature of the heating station 409. As the equilibrium takes place, the particle may experience physical changes due to the increased temperature. The physical changes may include reductions in particle diameter, as well as a change in the complex index of refraction of the particle. Changes in a particles diameter and/or index of refraction may alter the amount and intensity of scattered light produced by a particle.

Thereafter, the particle may traverse the propagating light beam 407C provided by the light source 405C situated at the exit of the heating station 409, resulting in a light scattering 412. The resultant light scattering may be measured by light detector 411C, also situated at the exit of the heating station 409. It should be appreciated that particle measurements may be obtained as the particle is being heated via the heater of the heating station. Based on the intensity of the measured light scattering from the first light beam 407A in a region at ambient temperature and the measured light scattering from the second beam 407B or 407C in a region at an elevated temperature with the heating station, or data, changes in the particles diameter and index of refraction may be determined. The light detectors 411A-C may be configured to send the measured data 418 to a particle identifier 413 in the form of an analog electrical signal. It should be appreciated that the temperature variation may be applied to the particle in situ.

The particle identifier 413 may include a quantizing unit 417, which may receive the measured data 418 and a current atmosphere temperature 420 of the heating station 409. The quantizing unit 417 may quantify the optical scattering, or measured data 418, associated with the particle 401 as a function of temperature of the heating station 420. The temperature 420 of the heating station is assumed to be approximately the temperature of the particle once the particle has reached equilibrium in the heating station (601 in FIG. 5). The quantizing may further involve determining an estimated particle index of refraction or diameter, or an estimated decrease of index of refraction or diameter, based on the given temperature 420. The quantization may result in quantized information 422.

The quantized information 422 may thereafter be sent to a characterizing unit 419. The characterizing unit may characterize the change in size, or index of refraction, of the particle as a function of the optical scattering, or measured data 418 (603 in FIG. 5). The characterization may further include searching through a database of estimated particle index of refractions or diameters, or estimated decreases of index of refractions or diameters for different particles given the temperature 420. The characterizing may provide characterization data 424.

The characterization data 424 may thereafter be sent to a identifying unit 421. The identifying unit 421 may identify the particle based on a characterized change in the size or index of refraction, or estimated values of the same, of the particle (605 in FIG. 5). The identifying unit 421 may thereafter provide a particle identification result 265 shown in FIG. 3.

The particle identifier 413 may be configured to send the quantized information 422, the characterized data, and/or the particle identification result 265 to a routing unit 239. The routing unit 239 may act as an intermediary between the particle identifier 413 and various network components 246. It should be appreciated that the routing unit 239 need not be employed, and the particle identifier 413 may instead be directly connected to the various network components 246.

The routing unit 239 may be configured to send measurement instructions 245 to the particle identifier 413. The measurement instructions 245 may include, for example, on/off instructions or calculation parameters to be utilized by the quantizing 417 or characterizing 419 units. The particle identifier 413 and the routing unit 239 may be connected via a connection link 241. It should be appreciated that the connection link 241 may be a wired, optical, or wireless connection, or any other data transfer connection known in the art.

The routing unit 239 may also be connected to a database storage 247. The routing unit 239 may send the database storage 247 a particle identification request, and/or a data storage request 251. The particle identification request may include a retrieval request of stored data via the quantizing 417, characterizing 419, and/or identifying 421 units, where the retrieved data may be used for processing. The particle identification request may further include a request to compare information stored in the database storage 247 with information obtained or calculated by the particle identifier 413 for the purpose of quantizing, characterizing, and/or identifying the particle. The data storage request 251 may include may include a request to store data obtained or calculated by the particle identifier 413.

The database storage 247 may send a particle identification result 253 to the routing unit 239. The particle identification result 253 may be any form of data that may be requested by the particle identifier 413. The routing unit 239 may, in turn, send all incoming messages or signals to the particle identifier 413.

The routing unit 239 may also be coupled to a network 255. The routing unit 239 may send a particle identification request, data storage request, and/or data sharing request 259 to the network 255. The particle identification request and data sharing request 259 may be similar to the request 251 sent to the database storage 247. The data sharing request 259 may be a request to share data with a user 269 that may be connected to the network 255, or another detection system 271 that may be connected to the network 255. The network 255, or more specifically, a server or other network element (not shown) connected to the network 255, may also send a message 261 in the form of particle identification results, similar to the result 253 sent by the database storage 247, or instructions to the routing unit 239. The instructions 261 may comprise measurement instructions similar to the instructions 245 sent to the particle identifier 413.

The database storage 247 and the network 255 may also include a bidirectional data transfer connection 263. The database storage 247 may send identification results and/or a data sharing request 265 to the network 255. The network 255 may send an identification request 267 to the database storage 247. It should be appreciated that the data transfer connections 249, 257, and 263 between the routing unit and the data storage, the routing unit and the network, and the network and the data storage, respectively, may include or be supported by any data transmission link known in the art.

FIG. 6 illustrates a single-particle, multi-stage detection system 700 according to example embodiments. The particle detection system 700 may feature a number of heating stations referenced as 409A through 409N. It should be appreciated that while the example provided by FIG. 6 only illustrates three heating stations, any number of heating stations may be utilized in a single particle, multi-stage, detection system.

Similarly to the heat station of FIG. 3, each heating station 409A-409N of FIG. 6 may include a light source 425A-425N that may be configured to provide a propagating light beam 429A-429N, respectively. Each heating station 409A-409N may also include a light detector 427A-427N that may be configured to detect scattered light resulting from the particle traversing the propagating light beam 429A-429N, respectively. Each light detector 427A-427N may also be in connection with the particle identifier 413 via connections 415A-415N, respectively. It should be appreciated that the multi-stage detection system 700 may also be connected to various network components 246 via a connection 241, as described above in reference to FIG. 3. It should further be appreciated that although the heating stations of FIG. 6 illustrate a single light source and light detector pair, each heating station may include any number of light source and light detector pairs, for example as shown in FIG. 3.

Utilizing the various heating stations of FIG. 6, the gradual impact of temperature change may be measured for a single particle as it traverses through the various heating stages. In a multi-stage system, the quantizing 417, characterizing 419, and identifying 421 units of the particle identifier 413 may provide calculations as a function of the various temperatures the particle will be exposed to via the respective heating stations. Thus, in contrast to prior art particle detection systems, the single particle multi-stage detection system 700 may provide information on a single particle as that same particle experiences a variety of temperature increases. Unlike the prior art, bulk sample volumes, detection system of FIG. 2, the single-particle, multi-stage, detection system 700 according to an example embodiment eliminates the unreliability presented by bulk sample volumes.

Figure 7:
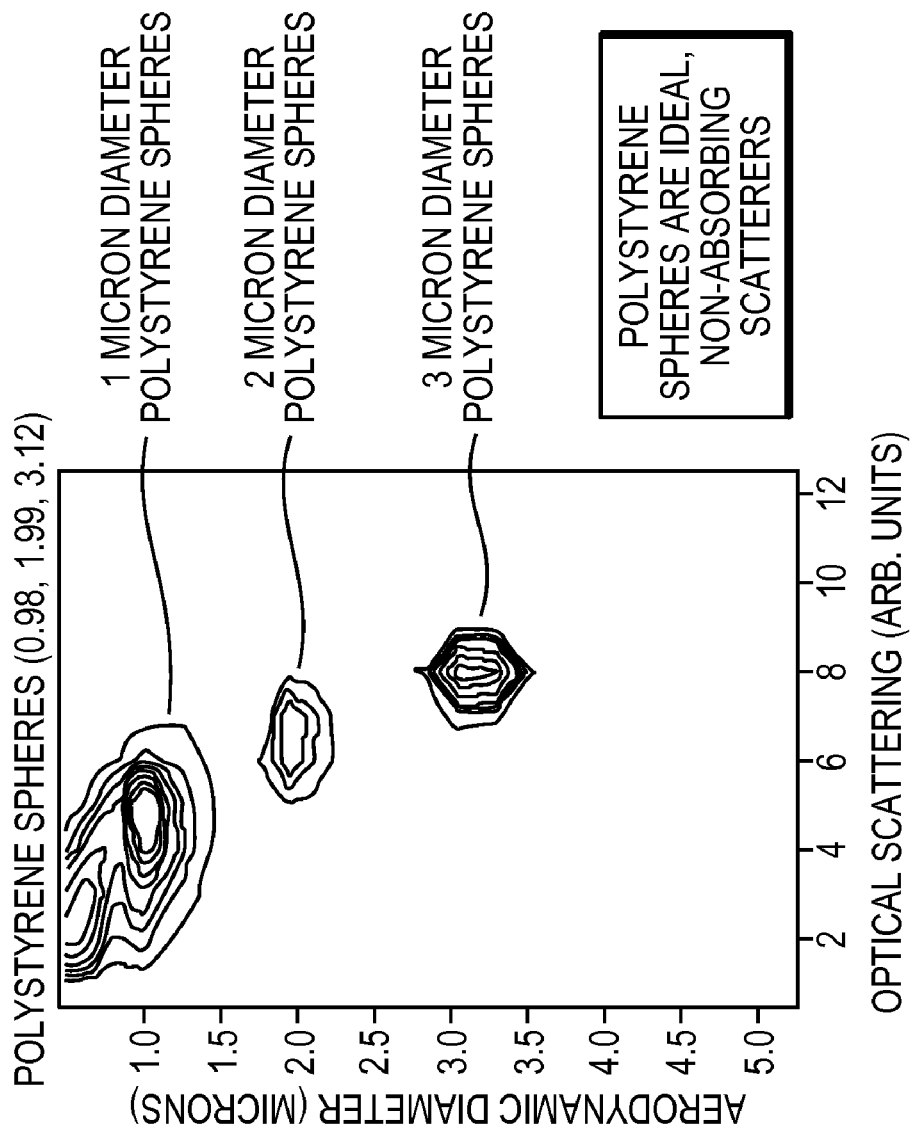
FIGS. 7-9 are plots of experimental data obtained using the system of FIGS. 3 and 4.
Figure 8:
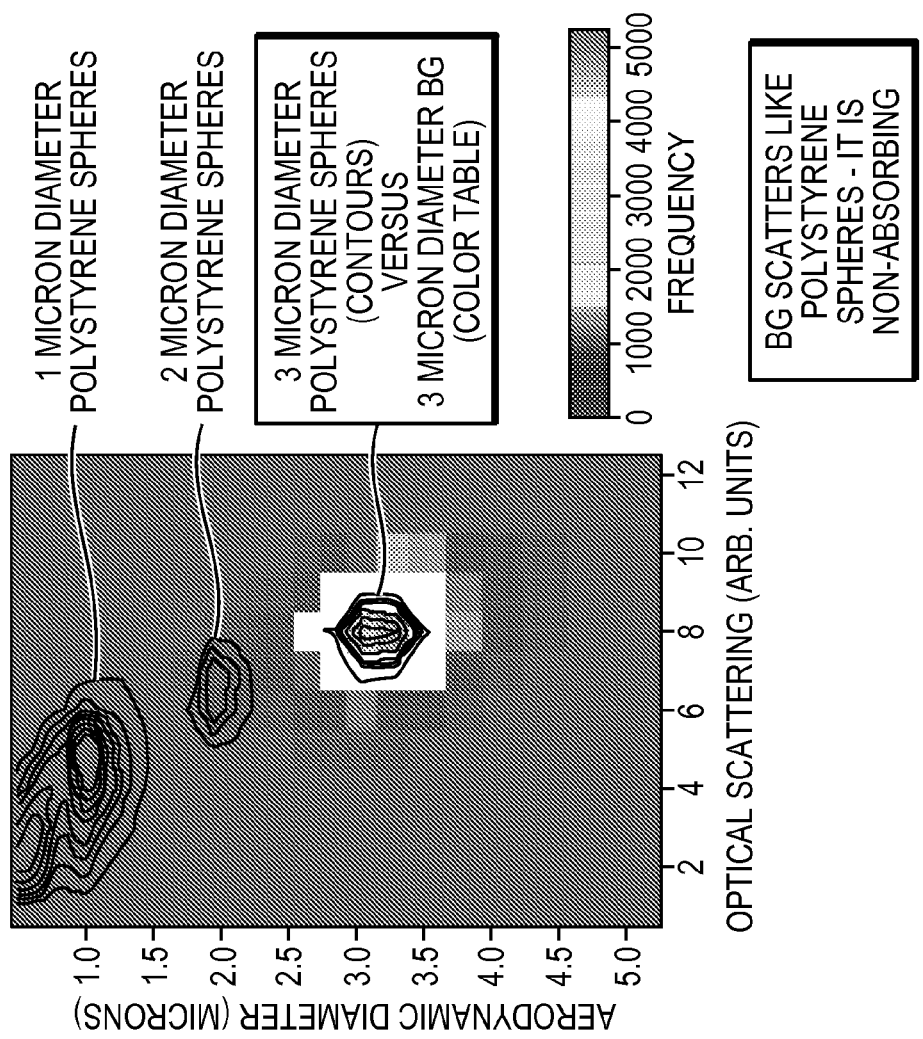
Figure 9:
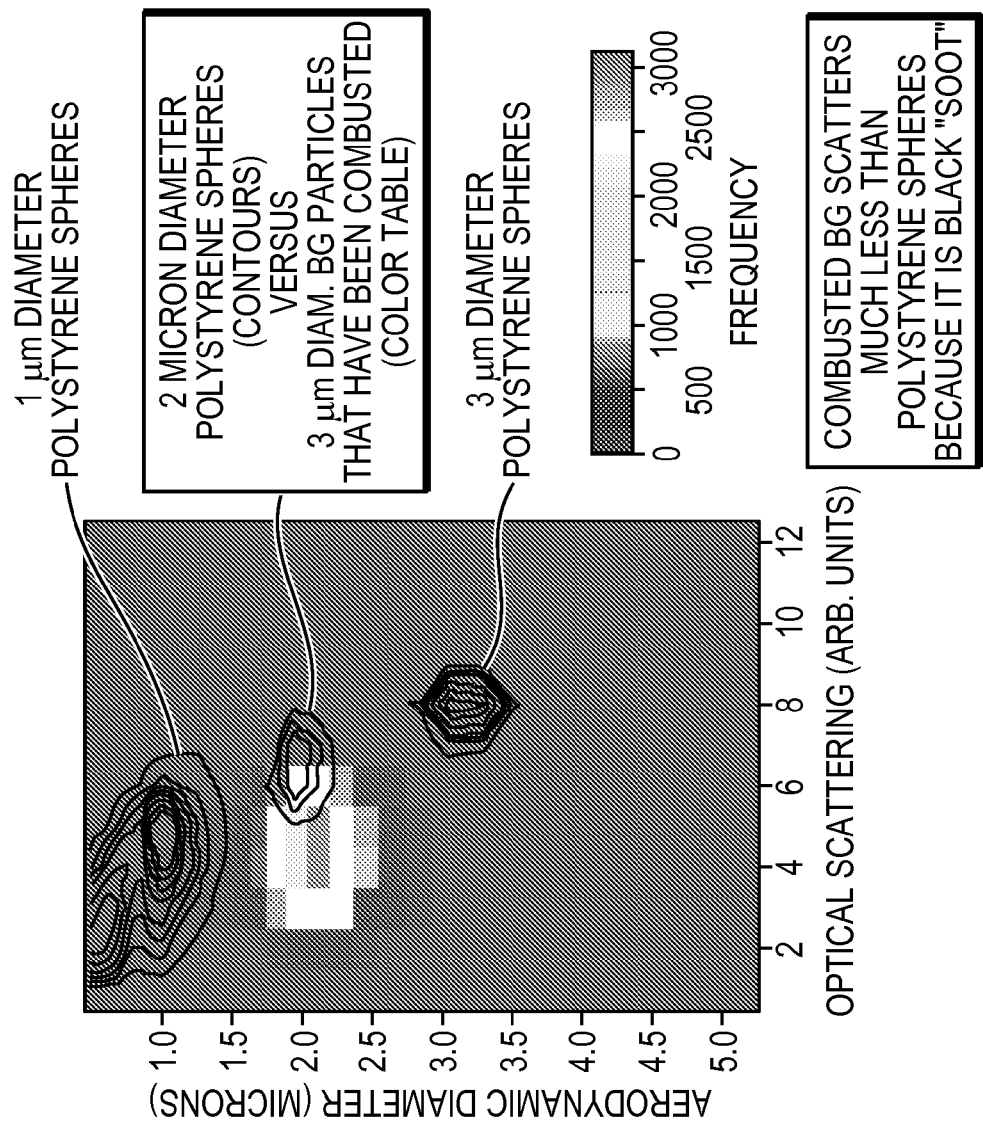

FIGS. 7-9 illustrate examples of cumulative data and analysis that may be obtained via the single particle detection systems described in FIGS. 3-6. FIG. 7 provides an example of an effect of optical scattering (x-axis) with respect to aerodynamic particle size (y-axis). In FIG. 7, optical scattering and aerodynamic particle size data (shown as contoured lines) for three polystyrene particles, including diameters of 1 µm, 2 µm, and 3 µm, is illustrated. As shown, as the particle size increases, the amount of optical scattering provided by the particle also increases as does the particle's aerodynamic diameter. By evaluating the behavior of a particle due to temperature change, the identity of the particle may be determined. It should be appreciated that polystyrene particles were used in the present example for their ability of providing non-absorbing light scattering, thereby greatly highlighting the differences in optical scattering versus particle diameter size. Systems according to various example embodiments are not limited to polystyrene particles or their general class of particle or materials producing the particles.

Similar to FIG. 7, FIG. 8 illustrates an effect of optical scattering and aerodynamic diameter due to particle size of the three polystyrene particles including diameters of 1 μm, 2 μm, and, 3 μm shown as contoured lines. FIG. 8 also illustrates the optical scattering properties of a 3 μm organic particle (Bacillus Globigii, or BG) which is shown via a frequency plot. Note that the results provided in FIG. 8 are obtained without the use of an elevated temperature. Therefore, as one may expect, the inorganic and organic particles including the same diameter (3 μm) provide similar optical scattering results and similar aerodynamic scattering results.

FIG. 9 illustrates the optical scattering and aerodynamic diameter properties of the Bacillus Globigii, or BG particles described above in reference to FIG. 8 upon undergoing a temperature variation. The optical scattering and aerodynamic diameter data of the three sizes of polystyrene particles (polystyrene particles with diameters of 1 μm, 2 μm, and 3 μm) are repeated from FIG. 8 for reference. The optical scattering property of the organic particle (3 μm BG particle) has reduced in size and, therefore, provides a reduced amount of optical scattering. It should further be appreciated that the reduction in the produced optical scattering may also be caused by a darkening of the inorganic particle due to the temperature variation. As a particle combusts, or is near combustion, the particle may appear as or exhibit properties of black soot, thereby lessening the amount of optical scattering. It should also be appreciated that the 3 μm combusted organic particles provide aerodynamic diameter values which are similar to 2 μm polystyrene sphere particles but optical scattering values more similar to 1 μm polystyrene sphere particles.

It should be appreciated that the example embodiments presented herein may be used to discriminate any type of aerosol. An aerosol may be an organic, inorganic, or biological particle, or any particle known in the art. It should further be appreciated that example embodiments may be utilized to discriminate between particles of a same type (e.g., distinguishing between two organic particles) and/or between particles of a different type (e.g., distinguishing between an organic and inorganic particle).

It should be understood that certain processes, in part or in their entireties, such as the particle detection or identification process, disclosed herein, may be implemented in hardware, firmware, or software. If implemented in software, the software may be stored on any form of computer readable medium, such as random access memory (RAM), read only memory (ROM), compact disk read only memory (CD-ROM), and so forth. In operation, a general purpose or application specific processor loads and executes the software in a manner well understood in the art.

While this invention has been particularly shown and described with references to example embodiments thereof, it will be understood by those skilled in the art that various changes in form and details may be made therein without departing from the scope of the invention encompassed by the appended claims.

What is claimed is:

1. A method for identifying a particle in a flow, comprising:
   at each of multiple temperatures above ambient temperature, quantifying an optical scattering of the particle as a function of particle temperature, the particle temperature being at or near a temperature of atmosphere surrounding the particle;
   characterizing a physical change of the particle as a function of the optical scattering as quantified across the multiple temperatures; and
   identifying the particle based on a characterized physical change of the particle.

2. The method of claim 1 wherein the physical change is a change in diameter size and/or index of refraction of the particle.

3. The method of claim 1 wherein quantifying the optical scattering further includes quantifying the optical scattering in a non-binary manner.

4. The method of claim 1 wherein quantifying the optical scattering further includes detecting the optical scattering with a single light detector.

5. The method of claim 1 wherein characterizing a change in size of the particle further includes characterizing the change as a function of a measure of the particle's aerodynamic diameter.

6. The method of claim 1 wherein quantifying, characterizing, and identifying is performed while the particle is in situ.

7. The method of claim 1 wherein a maximum temperature of the multiple temperatures is at least a temperature at which the particle approaches combustion or vaporization.

8. The method of claim 1 further including causing the multiple temperatures to include a series of temperatures arranged in an increasing order.

9. The method of claim 1 further including activating a series of independent heating stations to provide the multiple temperatures.

10. The method of claim 9 wherein the quantifying, characterizing, and identifying occur after the particle passes through each heating station.

11. The method of claim 9 further including providing each heating station with a single light sensor, light source, and heat source.

12. A particle identifier for identifying a particle in a flow comprising:
   a quantifying unit configured to quantify an optical scattering of the particle as a function of particle temperature at each of multiple temperatures above ambient temperature, the particle temperature being at or near a temperature of atmosphere surrounding the particle;
   a characterizing unit configured to characterize a physical change of the particle as a function of the optical scattering as quantified across the one or more temperatures; and
   an identifying unit configured to identify the particle based on characterized physical change of the particle.

13. The identifier of claim 12 wherein the physical change is a change in diameter size and/or index of refraction of the particle.

14. The identifier of claim 12 wherein the quantifying unit is further configured to quantify the optical scattering in a non-binary manner.

15. The identifier of claim 12 wherein the quantifying unit is further configured to receive optical scattering data from a single detector.

16. The identifier of claim 12 wherein the characterizing unit is further configured to characterize the change in size of the particle as a function a measure of the particle's aerodynamic diameter.

17. The identifier of claim 12 wherein the particle is in situ.

18. The identifier of claim 12 wherein a maximum temperature of the multiple temperatures is at least a temperature at which the particle approaches combustion or vaporization.

19. The identifier of claim 12 wherein the multiple temperatures are provided with a series of independent heating stations arranged in order of increasing temperature.

20. The identifier of claim 19 wherein the quantifying unit, characterizing unit, and identifying unit are configured to quantify, characterize, and identify, respectively, the particle after the particle passes through each heating station.

21. The identifier of claim 19 wherein each heating station includes a single light sensor, light source, and heat source.

22. An identification system for identifying a particle in a flow, comprising:
   one or more heating stations disposed in the flow, each heating station including a sensor, a light source, and a heater, the heater being configured to heat an atmosphere in the heating station to a respective temperature so as to heat the particle to the respective temperature; and a particle identifier in communication with the one or more heating stations, the particle identifier configured to quantify an optical scattering produced by the particle at the respective temperature in each heating station, the particle identifier further configured to characterize a physical change of the particle exiting each of the one or more heating stations as a function of the respective temperature and optical scattering, the particle identifier further configured to identify the particle based on a characterized physical change of the particle across the one or more heating stations.

23. The system of claim 22 wherein the physical change is a change in diameter size and/or index of refraction of the particle.

24. The system of claim 22, further including plural heating stations arranged in order of increasing respective temperatures.

25. A method of identifying a particle in a flow, comprising:

providing multiple heating stations disposed in the flow;

heating an atmosphere in each heating station to a respective temperature;

admitting the particle to each heating station so as to heat the particle to each respective temperature;

detecting optical scattering of the particle produced by the particle in situ at each heating station;

quantifying the optical scattering with a particle identifier operably coupled to each heating station;

characterizing a physical change of the particle as a function of the respective temperature and optical scattering; and identifying the particle based on a characterized physical change of the particle across the multiple heating stations.

26. The method of claim 25 wherein the physical change is a change in diameter size and/or index of refraction of the particle.

27. The method of claim 25, wherein providing the multiple heating stations includes arranging the heating stations in order of increasing respective temperatures.

28. The system of claim 22, wherein each of the one or more heating stations is further configured to admit a single particle at a time.

29. The method of claim 25, further comprising:

admitting a single particle at a time to each heating station.

* * * * *